United States Patent [19]

Berner

[11] Patent Number: 4,931,549
[45] Date of Patent: Jun. 5, 1990

[54] PROCESS FOR ARYL-QUINONE AND ARYL-NAPHTHOQUINONE DIAZIDE SULFONIC ACIDS

[75] Inventor: Paul Berner, East Greenwich, R.I.

[73] Assignee: Hoechst Celanese Corporation, Somerville, N.J.

[21] Appl. No.: 29,843

[22] Filed: Mar. 24, 1987

[51] Int. Cl.$^5$ ............................................. C07C 113/00
[52] U.S. Cl. ..................................... 534/557; 531/556; 531/565
[58] Field of Search .......................... 534/556, 557, 565

[56] References Cited

U.S. PATENT DOCUMENTS

| | | | |
|---|---|---|---|
| 737,967 | 9/1903 | Schmidt | 534/557 X |
| 2,812,321 | 11/1957 | Eberhart et al. | 534/558 X |
| 2,861,064 | 11/1958 | Suckfull et al. | 534/557 |

OTHER PUBLICATIONS

Bartos, et al, Chemical Abstracts, vol. 95, #6911f (1981).

Primary Examiner—Floyd D. Higel
Attorney, Agent, or Firm—Hugh C. Crall

[57] ABSTRACT

A process for the preparation of aryl-diazide-sulfonic acids by a series of sequential in-situ process steps. The process comprises the nitrosation of a hydroxyarylsulfonic acid; conversion of the nitroso-derivative to a sulfamate which is then diazotized to the diazide. Temperature and pH are maintained in predetermined ranges to maintain the reaction products in solution without the formation side-products or the need to isolate intermediates.

The process of the invention is particularly useful in the preparation of light-sensitive materials such as naphthoquinonediazide sulfonic acids which are used in the preparation of photoresist compositions. The invention provides a high purity product at a high material efficiency, high equipment utilization, low effluent discharge, and reduced cost.

15 Claims, No Drawings

PROCESS FOR ARYL-QUINONE AND ARYL-NAPHTHOQUINONE DIAZIDE SULFONIC ACIDS

BACKGROUND OF THE INVENTION

This invention is process for preparing light sensitive aryl-diazide-sulfonic acids. These compounds are useful as chemical intermediates in the preparation of photoresist compositions; see, for example: *Light Sensitive Systems;* Kosar, Jr.; Chapter 7.4, John Wiley & Sons, NY, NY 1965, which is incorporate herein by reference.

Typically, in the prior art, light sensitive aryl-diazide-sulfonic acids are prepared by first nitrosating a hydroxy-substituted benzene or naphthalene sulfonic acid in dilute aqueous acid solution by the addition of sodium nitrite. The nitroso compound is then isolated as a precipitate and washed to remove unreacted starting materials and impurities. The nitroso intermediate is then reduced to an amine intermediate using sodium borohydride or sodium dithionite. The amine intermediate is recovered as a precipitate and washed to remove unreacted starting materials and impurities. The amine is then reslurried in water and contacted with sodium nitrite at low pH to form the diazide compound.

In contrast to above multistep, multi-reactor process of the prior art, the process of this invention eliminates the need to isolate and purify the intermediates which are maintained in aqueous solution. Impurities, unreacted starting materials etc. are removed by filtration of reaction medium. In this manner, high productivity, high yield and reduced costs are achieved by removing the impurities which are present in small quantities as precipitates—not as was done in the prior art, isolating and purifying the intermediate reaction products. Additional advantages include increased yield, high product purity, high reactor utilization and reduced waste discharge streams.

SUMMARY OF THE INVENTION

This invention is a process for the preparation of light sensitive, aryl-diazides-sulfonic acids and their salts. These compounds are useful in the preparation of chemical intermediates for producing light sensitive compositions; in particular, light sensitive photoresists compositions which find wide application in the preparation of electronic circuity and lithographic printing and proofing plates.

Aryl-diazide-sulfonic acids prepared according to the process of this invention may be represented by the general formula:

$$R_x-A-(SO_3M)_y \qquad I$$

wherein A represents an aryl group of the quinonediazide or a naphthoquinonediazide structure containing an oxo (O=) anion and a diazo (N$_2$=) cation. R represents a monovalent substituent selected from halogen, nitro and lower alkyl; X represents an integer from 0 to 3, y an integer from 1 to 3 and M represents a hydrogen atom metal.

The aryl-diazide-sulfonic acids of the above formula are prepared according to the process of the invention from hydroxy-substituted benzene and naphthalene sulfonic acids having the formula:

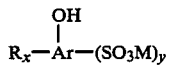

$$\overset{OH}{\underset{R_x-Ar-(SO_3M)_y}{|}}$$

wherein Ar represents a benzene or naphthalene nucleus and the terms R, M, x, y have the meaning set forth above Quinone and naphthoquinonediazide sulfonic acids or their salts are prepared, according to the process of invention by the following general procedure:

(1) nitrosating the ring of the moiety designated—Ar;
(2) reducing the nitroso intermediate of step (1) at an alkaline pH to convert the nitroso substituent to its sulfamate derivative;
(3) mixing the sulfamate derivative with diazotizing reagent under non-reactive conditions; and
(4) acidifying the sulfamate—diazotizing reactant solution to effect diazotization of the sulfamate substituent and formation of the aryl diazide sulfonic acid.

DESCRIPTION OF THE PREFERRED EMBODIMENTS

This invention is a process for the preparation aryl-diazide-sulfonic acids. These compounds may be represented by the following general formula:

$$R_x-A-(SO_3M)_y \qquad (I)$$

wherein:

R represents a monovalent substituent selected from halogen, nitro, and lower alkyl of 1 to 6 carbons; x is an integer from 0 to 3;

A represents an aryl group of the quinonediazide or naphthoquinonediazide structure containing an oxo (O=) anion and a diazonium cation (N$_2$=);

M represents a hydrogen atom metal; and y represents an integer from 1 to 3.

Examples of the aryl-diazide-sulfonic acids that may be prepared by the process of the invention are represented by the following formulae:

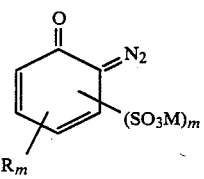

II

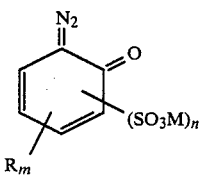

III

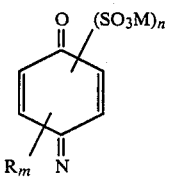

IV

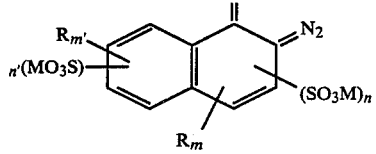

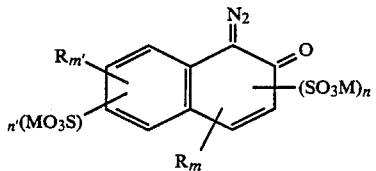

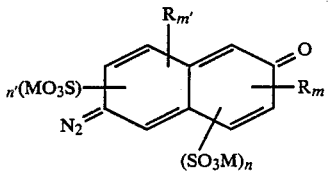

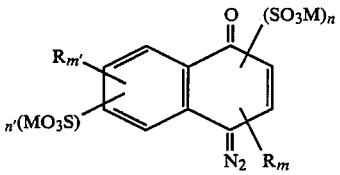

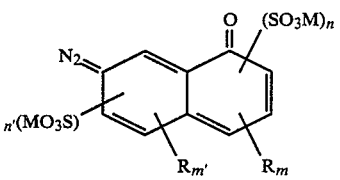

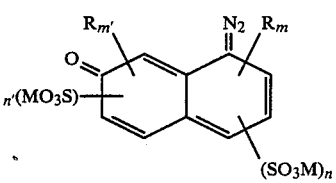

R and M are being as defined above m, m', n and n' being an integer from 0 to 3 which may be the same or different with the proviso that one (SO$_3$M) group is present in the structure.

Specific examples include benzoquinonediazidemonosulfonic acid, naphthoquinonediazidemonosulfonic acid, their nitro, chloro, bromo or alkyl nucleus-substituted compounds; and their sodium and, potassium and aluminium, trimethylammonium, triethylammonium, pyridinium, or N,N-dimethylanilinium salts.

Some more detailed examples follow: 1,4-benzoquinonediazide(4)-2-sulfonic acid, 1,4-benzoquinonediazide(4)-3-sulfonic acid, 2-methyl-1,4-benzoquinonediazide(4)-5-sulfonic acid, 2-methyl-1,4-benzoquinonediazide(4)-6-sulfonic acid, 2-isopropyl-1,4-benzoquinonediazide(4)-3-sulfonic acid, 2-chloro-1,4-benzoquinonediazide(4)-5-sulfonic acid, 2-chloro-1,4-benzoquinonediazide(4)-6-sulfonic acid, 2-bromo-1,4-benzoquinonediazide(4)-5-sulfonic acid, 2-bromo-1,4-benzoquinonediazide(4)-6-sulfonic acid, 2-nitro-1,4-benzoquinonediazide(4)-5-sulfonic acid, 2,6-dimethyl-1,4-benzoquinonediazide(4)-3-sulfonic acid, 2,6-dichloro-1,4-benzoquinonediazide(4)-3-sulfonic acid, 2,6-dibromo-1,4-benzoquinonediazide(4)-3-sulfonic acid, 2-chloro-6-nitro-1,4-benzoquinonediazide(4)-3-sulfonic acid, 2-fluoro-1,4-benzoquinonediazide(4)-5-sulfonic acid, 1,2-benzoquinonediazide(2)-3-sulfonic acid, 1,2-benzoquinonediazide(2)-4-sulfonic acid, 1,2-benzoquinonediazide( 2)-5-sulfonic acid, 1,2-benzoquinonediazide(2)-6-sulfonic acid, 4-nitro-1,2-benzoquinonediazide(2)-5-sulfonic acid, 4-chloro-1,2-benzoquinonediazide(2)-5-sulfonic acid, 4-bromo-1,2-benzoquinonediazide(2)-5-sulfonic acid, 6-chloro-1,2-benzoquinonediazide(2)-4-sulfonic acid, 6-bromo-1,2-benzoquinonediazide(2)-4-sulfonic acid, 6-chloro-1,2-benzoquinonediazide(2)-5-sulfonic acid, 6-bromo-1,2-benzoquinonediazide(2)-5-sulfonic acid, 4-methyl-1,2-benzoquinonediazide(2)-5-sulfonic acid, 4-methyl-1,2-benzoquinonediazide(2)-5-sulfonic acid, 5-methyl-1,2-benzoquinonediazide(2)-4-sulfonic acid, 3,5-dichloro-1,2-benzoquinonediazide(2)-4-sulfonic acid, 3,5,6-trichloro-1,2-benzoquinonediazide(2)-4-sulfonic acid, 4-nitro-6-chloro-1,2-benzoquinonediazide(2)-5-sulfonic acid, 1,2-benzoquinonediazide(2)-3,5-disulfonic acid, 1,2-naphthoquinonediazide(2)-3-sulfonic acid, 1,2-naphthoquinonediazide(2)-4-sulfonic acid, 1,2-naphthoquinonediazide(2)-5-sulfonic acid, 1,2-naphthoquinonediazide(2)-6-sulfonic acid, 1,2-naphthoquinonediazide(2)-7-sulfonic acid, 4-chloro-1,2-naphthoquinonediazide(2)-5-sulfonic acid, 3-bromo-1,2-naphthoquinonediazide(2)-5-sulfonic acid, 4-nitro-1,2-naphthoquinonediazide(2)-3-sulfonic acid, 6-nitro-1,2-naphthoquinonediazide(2)-4-sulfonic acid, 6-nitro-1,2-naphthoquinonediazide(2)-5-sulfonic acid, 1,2-naphthoquinonediazide(2)-3,6-disulfonic acid, 1,2-naphthoquinonediazide(2)-4,6-disulfonic acid, 1,2-naphthoquinonediazide(2)-4,6,8-trisulfonic acid, 2,1-naphthoquinonediazide(1)-4-sulfonic acid, 2,1-naphthoquinonediazide(1)-5-sulfonic acid, 2,1-naphthoquinonediazide(1)-6-sulfonic acid, 2,1-naphthoquinonediazide(1)-7-sulfonic acid, 2,1-naphthoquinonediazide(1)-8-sulfonic acid, 3-chloro-2,1-naphthoquinonediazide(1)-5-sulfonic acid, 6-chloro-2,1-naphthoquinonediazide(1)-4-sulfonic acid, 8-chloro-2,1-naphthoquinonediazide(1)-4-sulfonic acid, 3-bromo-2,1-naphthoquinonediazide(1)-4-sulfonic acid, 7-bromo-2,1-naphthoquinonediazide(1)-4-sulfonic acid, 6,8-dichloro-2,1-naphthoquinonediazide(1)-4-sulfonic acid, 6-nitro-2,1-naphthoquinonediazide(1)-4-sulfonic acid, 5-nitro-2,1-naphthoquinonediazide(1)-6-sulfonic acid, 2,1-naphthoquinonediazide(1)-3,6-disulfonic acid, 2,1-naphthoquinonediazide(1)-4,6-disulfonic acid, 1,4-naphthoquinonediazide(4)-5-sulfonic acid, 1,4-naphthoquinonediazide(4)-7-sulfonic acid, 7-chloro-1,4-naphthoquinonediazide(4)-7-sulfonic acid, 1,4-naphthoquinonediazide(4)-5,7-disulfonic acid, 1,7-naphthoquinonediazide(7)-3-sulfonic acid, 1,7-naphthoquinonediazide(7)-3,6-disulfonic acid, 1,6-naphthoquinonediazide(6)-3-sulfonic acid, 2,6-naphthoquinonediazide(6)-1,4-disulfonic acid, 2-nitro-1,4-naphthoquinonediazide(4)-7-sulfonic acid; and their sodium and, potassium, and trimethylammonium, triethylammonium, pyridinium, or N,N-dimethylanilinium salts.

In particular, 1,2-benzoquinonediazide(2)-4-sulfonic acid, 1,2-benzoquinonediazide(2)-5-sulfonic acid, 1,2-naphthoquinonediazide(2)-4-sulfonic acid, 1,2-naphthoquinonediazide(2)-5-sulfonic acid, 1,2-naphthoquinonediazide(2)-6-sulfonic acid, 1,2-naphthoquinonediazide(2)-7-sulfonic acid, 2,1-naphthoquinonediazide(1)-4-sulfonic acid, 2,1-naphthoquinonediazide(1)-5-sulfonic acid, 2,1-naphthoquinonediazide(1)-6-sulfonic acid, and 2,1-naphthoquinonediazide(1)-7-sulfonic acid; and their sodium, potassium calcium, or barium salts are preferably used. Especially preferred are 1,2-naphthoquinonediazide(2)-5-sulfonic acid and 1,2-naphthoquinone(2)-4-sulfonic acid and 2,1-naphthoquinonediazide(1)-4-sulfonic acid, and their sodium, potassium, calcium, or barium salts.

The aryl-diazide-sulfonic acids are prepared according to the process of the invention from hydroxy-substituted benzenesulfonic acids and hydroxy-substituted naphthalene-sulfonic acids. Specific examples include the hydroxybenzenemono-, di and trisulfonic acids, hydroxynaphthalenemono-, di and trisulfonic acids, their nitro, chloro, bromo, or alkyl nucleus-substituted compounds; and their sodium and, potassium, and trimethylammonium, triethylammonium, pyridinium or N,N-dimethylanilinum salts.

Some more detailed examples follow:

1-hydroxybenzene-2-sulfonic acid, 1-hydroxybenzene-3-sulfonic acid, 2-methyl-1-hydroxybenzene-5-sulfonic acid, 2-methyl-1-hydroxybenzene-6-sulfonic acid, 2-isopropyl-1-hydroxybenzene-3-sulfonic acid, 2-chloro-1-hydroxybenzene-5-sulfonic acid, 2-chloro-1-hydroxybenzene-6-sulfonic acid, 2-bromo-1-hydroxybenzene-5-sulfonic acid, 2-bromo-1-hydroxybenzene-6-sulfonic acid, 2-nitro-1-hydroxybenzene-5-sulfonic acid, 2,6-dimethyl-1-hydroxybenzene-3-sulfonic acid, 2,6-dichloro-1-hydroxybenzene-3-sulfonic acid, 2,6-dibromo-1-hydroxybenzene-3-sulfonic acid, 2-chloro-6-nitro-1-hydroxybenzene-3-sulfonic acid, 2-fluoro-1-hydroxybenzene-5-sulfonic acid, 1-hydroxybenzene-3-sulfonic acid, 1-hydroxybenzene-4-sulfonic acid, 1-hydroxybenzene-5-sulfonic acid, 1-hydroxybenzene-6-sulfonic acid, 4-nitro-1-hydroxybenzene-5-sulfonic acid, 4-chloro-1-hydroxybenzene-5-sulfonic acid, 4-bromo-1-hydroxybenzene-5-sulfonic acid, 6-chloro-1-hydroxybenzene-2-4-sulfonic acid, 6-chloro-1-hydroxybenzene-5-sulfonic acid, 6-bromo-1-hydroxybenzene-5-sulfonic acid, 6-nitro-1-hydroxybenzene-5-sulfonic acid, 4-methyl-1-hydroxybenzene-5-sulfonic acid, 4-methyl-1-hydroxybenzene-5-sulfonic acid, 5-methyl-1-hydroxybenzene-4-sulfonic acid, 3,5-dichloro-1-hydroxybenzene-4-sulfonic acid, 3,5,6-trichloro-1-hydroxybenzene-4-sulfonic acid, 4-nitro-6-chloro-1-hydroxybenzene-5-sulfonic acid, 1-hydroxynaphthalene-3,5-disulfonic acid, 1-hydroxynaphthalene-3-sulfonic acid, 1-hydroxynaphthalene-4-sulfonic acid, 1-hydroxynaphthalene-5-sulfonic acid, 1-hydroxynaphthalene-6-sulfonic acid, 1-hydroxynaphthalene-7-sulfonic acid, 4-chloro-1-hydroxynaphthalene-5-sulfonic acid, 3-bromo-1-hydroxynaphthalene-5-sulfonic acid, 4-nitro-1-hydroxynaphthalene-5-sulfonic acid, 6-nitro-1-hydroxynaphthalene-4-sulfonic acid, 6-nitro-1-hydroxynaphthalene-5-sulfonic acid, 1-hydroxynaphthalene-3,6-disulfonic acid, 1-hydroxynaphthalene-4,6-disulfonic acid, 1-hydroxynaphthalene-4,6,8-trisulfonic acid, 1-hydroxynaphthalene-4-sulfonic acid, 2-hydroxynaphthalene-5-sulfonic acid, 2-hydroxynaphthalene-6-sulfonic acid, 2-hydroxynaphthalene-7-sulfonic acid, 2-hydroxynaphthalene-8-sulfonic acid, 3-chloro-hydroxynaphthalene-5-sulfonic acid, 6-chloro-2-hydroxynaphthalene-4-sulfonic acid, 8-chloro-2-hydroxynaphthalene-4-sulfonic acid, 3-bromo-2-hydroxynaphthalene-4-sulfonic acid, 7-bromo-2-hydroxynaphthalene-4-sulfonic acid, 6,8-dichloro-2-hydroxynaphthalene-4-sulfonic acid, 6-nitro-2-hydroxynaphthalene-4-sulfonic acid, 5-nitro-2-hydroxynaphthalene-6-sulfonic acid, 2-hydroxynaphthalene-3,6-disulfonic acid, 2-hydroxynaphthalene-4,6-disulfonic acid, 1-hydroxynaphthalene-5-sulfonic acid, 1-hydronaphthalene-6-sulfonic acid, 1-hydroxynaphthalene-7-sulfonic acid, 7-chloro-1-hydroxynaphthalene-5,7-sulfonic acid.

In particular, 1-hydroxybenzene-4-sulfonic acid, 1-hydroxybenzene-5-sulfonic acid, 1-hydroxynaphthalene-4-sulfonic acid, 1-hydroxynaphthalene-5-sulfonic acid, 1-hydroxynaphthalene-6-sulfonic acid, 1-hydroxynaphthalene-7-sulfonic acid, 2-hydroxynaphthalene-4-sulfonic acid, 2-hydroxynaphthalene-5-sulfonic acid, 2-hydroxynaphthalene-6-sulfonic acid, and 2-hydroxynaphthalene-7-sulfonic acid; and their sodium, potassium salts are preferably used. Especially preferred are 1-hydroxynaphthalene-5-sulfonic acid, 1-hydroxynaphthalene-4-sulfonic acid, and 2,1-naphthoquinonediazide-4-sulfonic acid, and their sodium, potassium, salts.

In the process of the invention, an hydroxy-substituted benzene sulfonic acid or hydroxy-substituted naphthalene sulfonic acid is dissolved in a solvent, preferably water and the ring of said acids is nitrosated. The nitrosation is preferably conducted using sodium nitrite which is added to an acidified solution of the sulfonic acid.

The nitrosation may be conducted at a temperature of about 0° to about 40° C.; more preferably about 5° to about 20° C. and most preferably about 5° to about 15° C. The pH value of the reaction mixture during the nitrosation step should be in the range of about 1 to about 3, more preferably about 1 to about 2 and most preferably about 1.5.

The nitrosation step may be conducted by adding an aqueous solution of sodium nitrite to a solution of the hydroxy-substituted aromatic sulfonic acid which has been acidified with hydrochloric acid. At least one mole of sodium nitrite is used per mole of the aromatic sulfonic acid, generally an excess of the nitrosating agent is required. After completing the sodium nitrite addition, the reaction mixture is held under agitation for approximately ½ hour to about 1½ hours to complete the nitrosation. The time to complete the nitrosation being dependent upon the pH, temperature and excess of reactant employed. The nitroso-reaction product precipitates from solution.

After completing the nitrosation reaction, excess nitrite is destroyed by the addition of sulfamic acid and the pH increased to alkaline conditions by the addition of an alkaline reagent, e.g. sodium hydroxide, sodium carbonate, potassium hydroxide, potassium carbonate, lithium, hydroxide, etc. The pH of the reaction mixture is adjusted to an alkaline value, preferably about 8.5 to 9.5 and the nitroso derivative dissolves.

The second reaction step in the process is the conversion of the nitroso derivative of the aromatic sulfonic acid to the sulfamate derivative. The nitroso-derivative solution may be optionally clarified prior to the sulfamate conversion e.g. by filtration or centrifugation The sulfamate derivative may obtained by reacting the nitroso derivative with a metal sulfite, e.g. sodium, or potassium sulfite, preferably sodium sulfite. The metal sulfite may be added as a solid or solution, preferably as a solid. The sulfite addition is conducted under agitation and may be made fairly rapidly. After the sulfite is added, a nitroso-sulfite adduct is formed which precipitates from solution.

The reaction mixture is then heated to dissolve this precipitated adduct. A temperature from about 40°-60° C. is sufficient to dissolve the nitroso-sulfite adduct and to bring about the conversion to the sulfamate. The pH of solution should be maintained at about 9. to 9.5 during the sulfamate formation by the addition of acid e.g. hydrochloric acid or sulfuric acid. Preferably, the initial reaction temperature is held at about 45° to 50° C.; overheating could result in sulfonation of the ring. The pH value of the reaction mixture will begin to rise as the reaction proceeds and it maintained below about 9.5 by acid addition. The reaction temperature then is increased to 50°-60° C., preferably about 50°-55° C. to complete the reaction.

After the pH stabilizes indicating the completion of the conversion to the sulfamate, the mixture is cooled to about 10°-20° C. and the pH is adjusted to about 5.0 to 6, preferably about 5.5 to about 6.0. Excess sodium nitrite is then added to the sulfamate solution. At this pH, the nitrite and sulfamate are unreactive and they are thoroughly mixed. The solution is then acidified to a pH value of about 3.0 and the temperature is maintained at about 10° C. or less. At this pH unreacted nitroso-derivative, amine by-products and other impurities will form a precipitate and they are removed by clarifying the sulfamate-nitrite solution, e.g. by filtration or centrifugation.

The clarified solution is then further acidified to a pH of about 1 to about 1.5 by the addition of hydrochloric acid and maintained at a temperature of 10° C. or less. After completing the acid addition, the reaction temperature is increased to about 15°-20° C. and an exothermic reaction commences.

After the exothermic reaction subsides, the reaction mixture is held at a temperature of about 35°-50° C. and at a pH below 2.0; preferably about 40° C. and at pH of 0.5-1.0. Nitrite is added, if necessary, to maintain an excess to complete the diazotization. The reaction mixture is then cooled to about 10° C., inert inorganic salt (e.g. sodium chloride) is added and the solution is held for about 30 to 60 minutes while maintaining the pH of about 1. The diazide is then recovered, washed, and dried.

In the above reaction scheme, the mixing of the sulfamate and the diazotizing reactant before acidification to the lower pH range is important and it provides higher product yield and purity. The pre-mixing step provides that upon acidification to reaction pH for diazotization, preferential diazotization occurs before the sulfamate can be acid hydrolyzed to the insoluble amine derivative which is very difficult to diaotize.

The following reaction scheme illustrates the process of the invention:

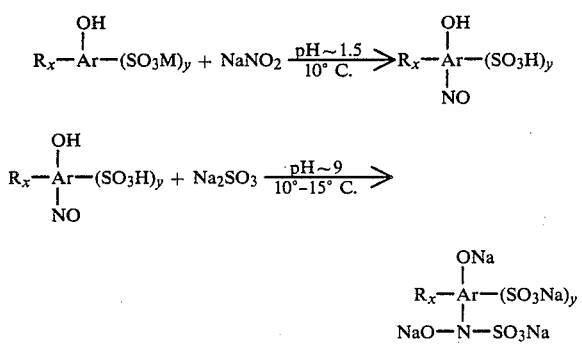

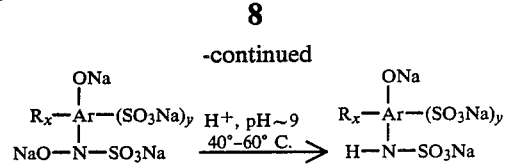

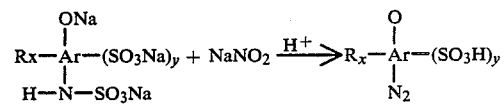

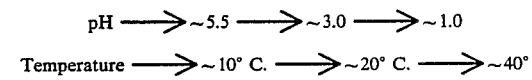

pH ⟶ ~5.5 ⟶ ~3.0 ⟶ ~1.0

Temperature ⟶ ~10° C. ⟶ ~20° C. ⟶ ~40° where R, Ar, M, x, y are as previously defined.

This process has the following advantages:
(1) The reaction is conducted in a series of sequential steps without the need to isolate intermediate reaction products.
(2) Stepwise acidification of the sulfamate solution allows removal of impurities before diazotization as precipitates and enhances the purity of the final product with minimal processing steps.
(3) Higher product yield and purity; higher productivity, reduced cost and reduced waste discharge streams.

The following example illustrates the invention:

EXAMPLE 1

Neville-Winters (N-W) Acid (56.0 grams 100% basis = 0.250 mol) is nitrosated in aqueous-hydrochloric acid solution at 10° C. and pH 1.5-2.0 by addition of an excess of a 20% sodium nitrite solution. After holding for approximately ½ hour, excess nitrite is destroyed by the addition of sulfamic acid and the pH is adjusted to about 9.0 at 10°-15° C. by addition of sodium carbonate, whereupon the nitroso compound dissolves.

Solid sodium sulfite is added over a 15 minute period at pH 9, whereupon the nitroso-sulfite adduct forms and precipitates out of solution. The reaction mixture is heated to 40°-45° C. at pH 9, whereupon the adduct starts to dissolve, and the pH begins to rise by itself.

The temperature is held at 42°-48° C. and the pH at 9.0-9.5 until the pH no longer rises by itself (approximately ½-1 hour). During this period the sulfamate is formed with the release of alkalinity, and hydrochloric acid must be added to hold the pH below 9.5.

The reaction mixture is then heated to 50°-55° C. and held in this range, adding more hydrochloric acid if needed to keep the pH below 9.5, until the pH no longer rises by itself (approximately 10 minutes).

The dark red sulfamate solution is then cooled to 10°-15° C., and the pH adjusted to 5.5-6.0 by addition of hydrochloric acid. At this point 20% sodium nitrite solution (approximately 3 mols $NaNO_2$ per mol N-W Acid) is added over ½ hour at 10°-15° C., holding the pH at about 5.5-6 by adding more hydrochloric acid if necessary and solids may separate from solution. The pH is then lowered to about 3.0 at 10° C. by addition of more hydrochloric acid, whereupon the color lightens and a precipitate separates. The mixture is clarified at 10° C. and pH 3.0, removing a greenish-yellow-by-product.

The clarified filtrate is weighed and re-charged into a beaker provided with a pH electrode and a basin for cooling/heating. The pH is lowered to 1.0-1.5, and the temperature increased to 15°-20° C. At this point the temperature rises by itself, and the pH falls off. The reaction is allowed to proceed without temperature control. At 20°-25° C. the diazide precipitates out and forms a thick mass of yellow needles. After the exothermic reaction subsides, the reaction mixture is heated to 40° C. and held for approximately 15 minutes, holding a positive nitrite test by adding more 20% sodium nitrite if needed and a pH of about 0.5 to 1.0 is maintained. The reaction mixture is then cooled to 20°-25° C., and approximately 5% of its weight of sodium chloride is added. The mixture is then cooled to 5°-7° C. and stirred for an additional hour, holding the pH at about 0.5-1.0 and the temperature at about 10° C.

The product is then recovered on a Buchner funnel and washed with two portions of cold, acidified 5-20% sodium chloride solution. The reaction yielded 57 grams of 1,2-naphthoquinonediazide(2)-4-sulfonic acid.

The process of this invention may be conducted by the batch or the continuous or semi-continuous methods. Essentially pure diazide compounds may be made by blocking the preferential nitrosating positions of the aromatic benzene or naphthalene rings with desired substituents e.g. the sulfonic acid group, the lower alkyl group, bromo, chloro, nitro etc. which is readily apparent to one of ordinary skill in the art. In the alternative, the process of the invention may be used to make isomeric diazide mixtures which may be used as such or separated into essentially pure compounds by known methods.

It should be understood that the invention is not limited to the particular embodiments shown and described herein but that various changes and modifications may be made without departing from the spirit and scope of the invention as defined by the following claims.

We claim:

1. A process for the preparation of an aryl-diazidesulfonic acids represented by the formula:

$R_x$—A—$(SO_3M)_y$ where A represents a aryl group of the quinone diazide or a naphthoquinonediazide structure containing an oxo (O=) anion and a diazonium ($N_2$=) cation, R represents a monovalent substituent selected from halogen, nitro, and lower alkyl of 1-6 carbons, x represents an integer from 0 to 3, y represents an integer from 1 to 3 and M represents a hydrogen atom, said diazide sulfonic acid being prepared from a hydroxy-substituted aryl sulfonic acid represented by the formula:

$$\underset{R_x-Ar-(SO_3M)_y}{\overset{OH}{|}}$$

wherein R, M, x and y are as defined above, Ar is an benzene or naphthalene nucleus, which comprises:
(a) nitrosating the ring of said benzene or naphthalene nucleus in a solvent at a pH from about 1 to 3, at a temperature from about 0° to 40° C. to introduce a nitroso substituent into said ring;
(b) converting said nitroso substitutent of said nitroso-substituted aryl sulfonic acid to a sulfamate substituent by contacting said nitroso-substituted aryl sulfonic acid with a metal sulfite at a pH value of about 8.5 to 9.5, and raising the reaction temperature to about 45° to 60= C.;
(c) mixing the reaction product of step (b) with a diazoting agent under weakly acidic pH and nonreactive temperature conditions to form a uniform mixture of said reaction product and said diazotizing agent and;
(d) acidifying said uniform mixture to diazotize said sulfamate substituent to form said aryl-diazide-sulfonic acid.

2. A process according to claim 1 wherein said hydroxy-substituted sulfonic acid is a hydroxy-substituted benzene sulfonic acid.

3. A process according to claim 2 wherein said hydroxy-substituted sulfonic acid is a 1-hydroxybenzene-4-sulfonic acid.

4. A process according to claim 2 wherein said hydroxy-substituted sulfonic acid is a 1-hydroxybenzene-5-sulfonic acid.

5. A process according to claim 2 wherein said hydroxy-substituted sulfonic acid is a 1-hydroxybenzene-6-sulfonic acid.

6. A process according to claim 2 wherein said hydroxy-substituted sulfonic acid is a 1-hydroxybenzene-7-sulfonic acid.

7. A process according to claim 2 wherein said hydroxy-substituted sulfonic acid is a 2-hydroxybenzene-4-sulfonic acid.

8. A process according to claim 1 wherein said hydroxy-substituted sulfonic acid is a hydroxy-substituted naphthalene sulfonic acid.

9. A process according to claim 8 wherein said hydroxy-substituted sulfonic acid is a 1-hydroxynaphthalene-4-sulfonic acid.

10. A process according to claim 8 wherein said hydroxy-substituted sulfonic acid is a 1-hydroxynaphthalene-5-sulfonic acid.

11. A process according to claim 8 wherein said hydroxy-substituted sulfonic acid is a 1-hydroxynaphthalene-6-sulfonic acid.

12. A process according to claim 8 wherein said hydroxy-substituted sulfonic acid is a 1-hydroxynaphthalene-7-sulfonic acid.

13. A process according to claim 8 wherein said hydroxy-substituted sulfonic acid is a 2-hydroxynaphthalene-4-sulfonic acid.

14. A process for preparing an aryl-diazide comprising
(a) mixing an aromatic compound selected from a hydroxy substituted benzene or naphthalane sulphonic acid containing at least one ring substituted sulfamate substituent with a diazotizing reagent under non-reactive conditions;
(b) forming an uniform mixture of said sulfamate substituted aromatic compound and said diazotizing reagent; and
(c) acidifying said uniform mixture to a pH value of less than 2 to effect diazotization of said sulfamate substituent.

15. A process according to claim 1 wherein prior to diazotizing, the pH is adjusted to about pH 3 and the reaction mixture is clarified to remove insolubles.

* * * * *

UNITED STATES PATENT AND TRADEMARK OFFICE
CERTIFICATE OF CORRECTION

PATENT NO. : 4,931,549

DATED : June 5, 1990

INVENTOR(S) : Paul Berner

It is certified that error appears in the above-identified patent and that said Letters Patent is hereby corrected as shown below:

Column 5, Line 5-6, the phrase should read beginning with the word sodium, -- sodium and potassium salts are preferably used. --

Column 5, Line 10, the phrase should read beginning with the word sodium, -- sodium and potassium salts. --

Column 8, Second Illustration, add another bond between the O and $N_2$

Column 10, Line 2 should read -- 45° to 60°C.

Signed and Sealed this

Tenth Day of March, 1992

Attest:

HARRY F. MANBECK, JR.

Attesting Officer      *Commissioner of Patents and Trademarks*